(12) United States Patent
Champagne et al.

(10) Patent No.: US 11,185,357 B2
(45) Date of Patent: Nov. 30, 2021

(54) DISTAL RADIUS PLATE

(71) Applicant: Exsomed Holding Company, LLC, Phoenix, AZ (US)

(72) Inventors: Lloyd P. Champagne, Phoenix, AZ (US); Jozef Zoldos, Phoenix, AZ (US)

(73) Assignee: ExsoMed Corporation, Aliso Viejo, CA (US)

( * ) Notice: Subject to any disclaimer, the term of this patent is extended or adjusted under 35 U.S.C. 154(b) by 179 days.

(21) Appl. No.: 16/596,315

(22) Filed: Oct. 8, 2019

(65) Prior Publication Data

US 2020/0214750 A1 Jul. 9, 2020

Related U.S. Application Data

(63) Continuation of application No. 15/146,824, filed on May 4, 2016, now Pat. No. 10,441,330.

(60) Provisional application No. 62/163,912, filed on May 19, 2015.

(51) Int. Cl.
*A61B 17/80* (2006.01)
*A61B 17/68* (2006.01)

(52) U.S. Cl.
CPC .......... *A61B 17/8061* (2013.01); *A61B 17/80* (2013.01); *A61B 17/8004* (2013.01); *A61B 17/809* (2013.01); *A61B 17/8014* (2013.01); *A61B 2017/681* (2013.01)

(58) Field of Classification Search
CPC ................ A61B 17/8061; A61B 17/80; A61B 2017/681
See application file for complete search history.

(56) References Cited

U.S. PATENT DOCUMENTS

| | | | |
|---|---|---|---|
| 1,741,279 | A | 12/1929 | Bowman |
| 2,037,586 | A | 4/1936 | Olson |
| 2,210,455 | A | 8/1940 | Hosking |
| 2,217,951 | A | 10/1940 | Hosking |
| 2,229,892 | A | 1/1941 | Hosking |

(Continued)

FOREIGN PATENT DOCUMENTS

| | | |
|---|---|---|
| CH | 643131 | 5/1984 |
| CH | 646858 | 12/1984 |

(Continued)

OTHER PUBLICATIONS

PCT; International Search Report and Written Opinion dated Sep. 17, 2010 in Application No. PCT/US2009/046662.

(Continued)

*Primary Examiner* — Christian A Sevilla
(74) *Attorney, Agent, or Firm* — Knobbe, Martens, Olson & Bear, LLP

(57) ABSTRACT

A distal radius plate according to the invention is ergonomically formed to be more easily centered on the radius bone. The distal radius plate has two main portions: an elongated portion that attaches to the body of the radius and a distal radius portion that attaches to the lower most, wider portion of the radius bone. Because of its ergonomic shape the distal radius plate is fast and easy to center on the radius and install. In another embodiment, the distal radius plate may include a metal support that is partially or entirely covered with a plastic to eliminate or reduce detailed machining of the metal, which reduces part cost and manufacturing time.

20 Claims, 9 Drawing Sheets

(56) References Cited

U.S. PATENT DOCUMENTS

| | | | |
|---|---|---|---|
| 2,242,003 A | 5/1941 | Lorenzo | |
| 3,078,900 A | 2/1963 | Walker | |
| 3,275,055 A | 9/1966 | Gutshall | |
| 3,397,699 A | 8/1968 | Kohl | |
| 3,717,146 A | 2/1973 | Halloran | |
| 4,016,874 A | 4/1977 | Maffei | |
| 4,175,555 A | 11/1979 | Herbert | |
| 4,350,465 A | 9/1982 | Lovisek | |
| 4,380,414 A | 4/1983 | Capuano | |
| 4,463,753 A | 8/1984 | Gustilo | |
| 4,471,777 A | 9/1984 | McCorkle | |
| 4,584,722 A | 4/1986 | Levy et al. | |
| 4,608,965 A | 9/1986 | Anspach | |
| 4,653,487 A | 3/1987 | Maale | |
| 4,764,066 A | 8/1988 | Terrell | |
| 4,781,191 A | 11/1988 | Thompson | |
| 4,812,095 A | 3/1989 | Piacenti | |
| 4,820,235 A | 4/1989 | Weber et al. | |
| 4,842,463 A | 6/1989 | Landt | |
| 4,901,717 A | 2/1990 | Moore et al. | |
| 4,909,789 A | 3/1990 | Taguchi et al. | |
| 5,061,283 A | 10/1991 | Silvestrini | |
| 5,234,299 A | 8/1993 | Giannuzzi | |
| 5,312,255 A | 5/1994 | Bauer | |
| 5,345,927 A | 9/1994 | Bonutti | |
| 5,443,466 A | 8/1995 | Shah | |
| 5,522,846 A | 6/1996 | Bonutti | |
| 5,645,545 A | 7/1997 | Bryant | |
| 5,667,510 A | 9/1997 | Combs | |
| 5,690,633 A | 11/1997 | Taylor et al. | |
| 5,840,078 A | 11/1998 | Yerys | |
| 5,853,413 A | 12/1998 | Carter et al. | |
| 6,187,007 B1 | 2/2001 | Frigg | |
| 6,221,006 B1 | 4/2001 | Dubrul et al. | |
| 6,231,319 B1 | 5/2001 | Iida et al. | |
| 6,231,413 B1 | 5/2001 | Tsukamoto | |
| 6,306,140 B1 | 10/2001 | Siddiqui | |
| 6,394,725 B1 | 5/2002 | Dicke | |
| 6,475,242 B1 | 11/2002 | Bramlet | |
| 6,517,541 B1 | 2/2003 | Sesic | |
| 6,592,623 B1 | 7/2003 | Bowlin et al. | |
| 6,607,530 B1 | 8/2003 | Carl et al. | |
| 6,808,526 B1 | 10/2004 | Magerl et al. | |
| 7,037,309 B2 | 5/2006 | Well et al. | |
| 7,041,106 B1 | 5/2006 | Carver et al. | |
| 7,063,491 B2 | 6/2006 | French | |
| 7,334,976 B2 | 2/2008 | Dicke | |
| 7,465,135 B2 | 12/2008 | Fritsch | |
| 7,507,242 B2 | 3/2009 | Triplett et al. | |
| 7,604,659 B2 | 10/2009 | Lee | |
| 7,708,738 B2 | 5/2010 | Fourcault et al. | |
| 7,766,942 B2* | 8/2010 | Patterson | A61B 17/7011 606/261 |
| 7,988,724 B2 | 8/2011 | Salahieh et al. | |
| 8,011,866 B2 | 9/2011 | Harris | |
| 8,157,803 B1 | 4/2012 | Zirkie, Jr. | |
| 8,348,575 B2 | 1/2013 | Walther | |
| 8,398,687 B2* | 3/2013 | Vasta | A61B 17/8061 606/284 |
| 8,414,648 B2 | 4/2013 | Reiley | |
| 8,419,776 B2* | 4/2013 | Prandi | A61B 17/8004 606/282 |
| 8,518,042 B2* | 8/2013 | Winslow | A61B 17/8061 606/71 |
| 8,568,462 B2* | 10/2013 | Sixto, Jr. | A61B 17/8085 606/280 |
| 8,597,337 B2 | 12/2013 | Champagne | |
| 8,608,783 B2* | 12/2013 | Graham | A61B 17/8023 606/280 |
| 8,814,918 B2* | 8/2014 | Orbay | A61B 17/8085 606/286 |
| 8,852,253 B2 | 10/2014 | Mafi | |
| 8,864,804 B2 | 10/2014 | Champagne et al. | |
| 8,888,429 B2 | 11/2014 | Pamer | |
| 8,906,075 B2* | 12/2014 | Conley | A61B 17/8605 606/286 |
| 9,017,404 B2 | 4/2015 | Champagne et al. | |
| 9,046,120 B2 | 6/2015 | Phua | |
| 9,086,088 B2 | 7/2015 | Walther | |
| 9,175,715 B2 | 11/2015 | Babej | |
| 9,265,600 B2 | 2/2016 | Niese | |
| 9,480,515 B2 | 11/2016 | Champagne | |
| 9,539,084 B2 | 1/2017 | Champagne | |
| 10,098,680 B2 | 10/2018 | Champagne | |
| 10,441,330 B2 | 10/2019 | Champagne et al. | |
| 2001/0049529 A1 | 12/2001 | Cachia et al. | |
| 2002/0045897 A1 | 4/2002 | Dixon et al. | |
| 2002/0055747 A1 | 5/2002 | Cano et al. | |
| 2002/0055749 A1 | 5/2002 | Esnouf et al. | |
| 2002/0143337 A1 | 10/2002 | Orbay et al. | |
| 2002/0198527 A1 | 12/2002 | Muckter | |
| 2003/0014077 A1 | 1/2003 | Leung | |
| 2003/0083661 A1 | 5/2003 | Orbay et al. | |
| 2003/0130735 A1 | 7/2003 | Rogalski | |
| 2004/0193217 A1 | 9/2004 | Lubbers | |
| 2004/0210227 A1 | 10/2004 | Trail et al. | |
| 2004/0260288 A1 | 12/2004 | Means | |
| 2005/0075642 A1 | 4/2005 | Felt et al. | |
| 2005/0085824 A1 | 4/2005 | Castaneda | |
| 2005/0107791 A1 | 5/2005 | Manderson | |
| 2005/0143735 A1 | 6/2005 | Kyle | |
| 2006/0129153 A1 | 6/2006 | Klaue et al. | |
| 2006/0149249 A1 | 7/2006 | Mathoulin et al. | |
| 2006/0165506 A1 | 7/2006 | Panasik | |
| 2006/0195099 A1 | 8/2006 | Bottlang | |
| 2006/0271061 A1 | 11/2006 | Beyar | |
| 2006/0276790 A1 | 12/2006 | Dawson | |
| 2007/0027547 A1 | 2/2007 | Rydell et al. | |
| 2007/0135816 A1 | 6/2007 | Kropf et al. | |
| 2007/0282342 A1 | 12/2007 | Niederberger et al. | |
| 2007/0299449 A1 | 12/2007 | Allinniemi et al. | |
| 2008/0183220 A1 | 7/2008 | Glazer | |
| 2008/0219801 A1 | 9/2008 | Toenjes | |
| 2008/0249547 A1 | 10/2008 | Dunn | |
| 2008/0249574 A1 | 10/2008 | McCombs et al. | |
| 2009/0062868 A1 | 3/2009 | Casutt | |
| 2009/0299369 A1 | 12/2009 | Orbay et al. | |
| 2010/0106254 A1 | 4/2010 | Delsignore | |
| 2010/0121136 A1 | 5/2010 | Champagne | |
| 2010/0130978 A1 | 5/2010 | Orbay et al. | |
| 2010/0211115 A1 | 8/2010 | Tyber et al. | |
| 2010/0278614 A1 | 11/2010 | Bickford | |
| 2010/0312286 A1 | 12/2010 | Dell'Oca | |
| 2010/0324556 A1 | 12/2010 | Tyber et al. | |
| 2011/0009865 A1 | 1/2011 | Orfaly | |
| 2011/0130794 A1 | 6/2011 | Vaidya | |
| 2012/0083847 A1 | 4/2012 | Huebner et al. | |
| 2012/0136398 A1 | 5/2012 | Mobasser | |
| 2012/0191140 A1 | 7/2012 | Bonutti | |
| 2012/0209270 A1 | 8/2012 | Segina et al. | |
| 2012/0221104 A1 | 8/2012 | Altman et al. | |
| 2012/0253464 A1 | 10/2012 | Hwang et al. | |
| 2012/0253465 A1 | 10/2012 | Missos | |
| 2013/0012987 A1 | 1/2013 | Klein et al. | |
| 2013/0053961 A1 | 2/2013 | Darwin et al. | |
| 2013/0060333 A1 | 3/2013 | Gonzalez | |
| 2013/0131699 A1 | 5/2013 | Jiango et al. | |
| 2013/0138123 A1 | 5/2013 | Stone et al. | |
| 2013/0165979 A1 | 6/2013 | Greenberg et al. | |
| 2013/0190872 A1 | 7/2013 | Makower et al. | |
| 2013/0197592 A1 | 8/2013 | Mafi | |
| 2013/0245626 A1 | 9/2013 | Lavi et al. | |
| 2013/0245700 A1 | 9/2013 | Choinski | |
| 2013/0245762 A1 | 9/2013 | Van Kampen et al. | |
| 2013/0261662 A1 | 10/2013 | Mayer et al. | |
| 2013/0274879 A1 | 10/2013 | Champagne et al. | |
| 2013/0282058 A1 | 10/2013 | ElAttrache et al. | |
| 2013/0325011 A1 | 12/2013 | Cleveland et al. | |
| 2014/0025124 A1 | 1/2014 | Champagne et al. | |
| 2014/0067063 A1 | 3/2014 | Bonutti | |
| 2014/0257349 A1 | 9/2014 | Sudekum | |
| 2014/0276846 A1 | 9/2014 | Mauldin | |
| 2014/0336712 A1 | 11/2014 | Stmad et al. | |

(56) References Cited

U.S. PATENT DOCUMENTS

| | | |
|---|---|---|
| 2015/0066060 A1 | 3/2015 | Bojarski |
| 2015/0094722 A1 | 4/2015 | Champagne et al. |
| 2015/0094724 A1 | 4/2015 | Champagne et al. |
| 2015/0094777 A1 | 4/2015 | Champagne et al. |
| 2015/0173737 A1 | 6/2015 | Champagne et al. |
| 2015/0182325 A1 | 7/2015 | Champagne et al. |
| 2016/0030097 A1 | 2/2016 | Mildner |
| 2016/0256290 A1 | 9/2016 | Seavey et al. |
| 2016/0296263 A1 | 10/2016 | Champagne et al. |
| 2016/0296264 A1 | 10/2016 | Champagne et al. |
| 2017/0027577 A1 | 2/2017 | Kubiak et al. |
| 2017/0035553 A1 | 2/2017 | Champagne et al. |
| 2017/0049167 A1 | 2/2017 | Champagne et al. |
| 2017/0189090 A1 | 7/2017 | Champagne et al. |
| 2017/0196609 A1 | 7/2017 | Champagne et al. |
| 2017/0325827 A1 | 11/2017 | Champagne et al. |
| 2018/0021124 A1 | 1/2018 | Champagne et al. |
| 2019/0336185 A1 | 11/2019 | Champagne et al. |

FOREIGN PATENT DOCUMENTS

| | | | |
|---|---|---|---|
| DE | 2713386 | 11/1978 | |
| DE | 102007003645 | 7/2008 | |
| EP | 0597223 | 5/1994 | |
| EP | 1378205 | 1/2004 | |
| EP | 2606843 | 6/2013 | |
| GB | 2007099 | 5/1979 | |
| GB | 2181356 | 4/1987 | |
| WO | WO 1997/33537 | 9/1997 | |
| WO | WO 2004/093700 | 4/2004 | |
| WO | WO 2005/092226 | 10/2005 | |
| WO | WO 2006/105935 | 12/2006 | |
| WO | WO 2007/081601 | 7/2007 | |
| WO | WO 2007/109140 | 9/2007 | |
| WO | WO 2008/063156 | 5/2008 | |
| WO | WO 2010/151589 | 12/2010 | |
| WO | WO 2012/050424 | 4/2012 | |
| WO | WO-2012050424 A1 * | 4/2012 | ........... A61B 17/846 |
| WO | WO 2014/011933 | 1/2014 | |
| WO | WO 2014/089522 | 6/2014 | |
| WO | WO 2015/050895 | 9/2015 | |
| WO | WO 2015/050896 | 9/2015 | |
| WO | WO 2015/050898 | 9/2015 | |
| WO | WO 2015/050900 | 9/2015 | |
| WO | WO 2015/050902 | 9/2015 | |
| WO | WO 2016/186847 | 11/2016 | |

OTHER PUBLICATIONS

PCT; International Search Report and Written Opinion dated Sep. 9, 2013 in Application No. PCT/US2013/050155.
PCT; International Search Report and Written Opinion dated Sep. 30, 2014 in Application No. PCT/US2014/058472.
PCT; International Search Report and Written Opinion dated Dec. 10, 2014 in Application No. PCT/US2014/058463.
PCT; International Search Report and Written Opinion dated May 4, 2016 in Application No. PCT/US2016/030850.
EP; Examination Report dated May 30, 2011 in Application No. 09774002.1.
EP; Examination Report dated May 25, 2012 in Application No. 09774002.1.
EP; Examination Report dated Feb. 12, 2016 in Application No. 13742332.3.
EP; Examination Report dated Oct. 11, 2016 in Application No. 13742332.3.
EP; Notice of Allowance dated Apr. 12, 2018 in Application No. 13742332.3.
USPTO; Office Action dated Oct. 4, 2011 in U.S. Appl. No. 12/372,712.
USPTO; Office Action dated May 29, 2012 in U.S. Appl. No. 12/372,712.
USPTO; Office Action dated Mar. 22, 2013 in U.S. Appl. No. 12/372,712.
USPTO; Notice of Allowance dated Jul. 30, 2013 in U.S. Appl. No. 12/372,712.
USPTO; Office Action dated Mar. 21, 2012 in U.S. Appl. No. 12/480,676.
USPTO; Office Action dated Sep. 18, 2012 in U.S. Appl. No. 12/480,676.
USPTO; Office Action dated Sep. 24, 2013 in U.S. Appl. No. 12/480,676.
USPTO; Office Action dated Feb. 18, 2014 in U.S. Appl. No. 13/555,933.
USPTO; Notice of Allowance dated Jun. 25, 2014 in U.S. Appl. No. 13/555,933.
USPTO; Office Action dated Aug. 29, 2014 in U.S. Appl. No. 13/648,019.
USPTO: Office Action dated Oct. 5, 2015 in U.S. Appl. No. 13/940,173.
USPTO; Final Office Action dated May 23, 2016 in U.S. Appl. No. 13/940,173.
USPTO: Notice of Allowance dated Jul. 1, 2016 in U.S. Appl. No. 13/940,173.
USPTO: Office Action dated Nov. 4, 2016 in U.S. Appl. No. 14/503,119.
USPTO; Office Action dated Jun. 13, 2017 in U.S. Appl. No. 14/503,119.
USPTO: Office Action dated Dec. 9, 2015 in U.S. Appl. No. 14/640,657.
USPTO; Office Action dated May 23, 2016 in U.S. Appl. No. 14/640,657.
USPTO; Notice of Allowance dated Sep. 1, 2016 in U.S. Appl. No. 14/640,657.
USPTO: Office Action dated Jan. 27, 2017 in U.S. Appl. No. 14/503,157.
USPTO; Office Action dated Jun. 2, 2017 in U.S. Appl. No. 14/503,157.
USPTO: Office Action dated Feb. 27, 2018 in U.S. Appl. No. 14/503,157.
USPTO: Final Office Action dated Oct. 25, 2018 in U.S. Appl. No. 14/503,157.
USPTO; Office Action dated Sep. 22, 2015 in U.S. Appl. No. 14/503,228.
USPTO: Office Action dated May 2, 2016 in U.S. Appl. No. 14/503,228.
USPTO; Office Action dated Feb. 9, 2017 in U.S. Appl. No. 14/503,228.
USPTO; Final Office Action dated Aug. 31, 2017 in U.S. Appl. No. 14/503,228.
USPTO: Office Action dated Jun. 6, 2018 in U.S. Appl. No. 14/503,228.
USPTO; Office Action dated Apr. 10, 2017 in U.S. Appl. No. 14/641,024.
USPTO; Office Action dated Dec. 15, 2017 in U.S. Appl. No. 14/984,145.
USPTO: Final Office Action dated Jun. 26, 2018 in U.S. Appl. No. 14/984,145.
USPTO; Notice of Allowance dated Nov. 27, 2018 in U.S. Appl. No. 14/984,145.
USPTO: Office Action dated Mar. 5, 2018 in U.S. Appl. No. 14/993,972.
USPTO: Final Office Action dated Jul. 20, 2018 in U.S. Appl. No. 14/993,972.
USPTO; Office Action dated Feb. 21, 2018 in U.S. Appl. No. 15/151,252.
USPTO: Final Office Action dated Aug. 13, 2018 in U.S. Appl. No. 15/151,252.
USPTO; Notice of Allowance dated Sep. 18, 2018 in U.S. Appl. No. 15/151,252.
USPTO; Notice of Allowance dated Nov. 9, 2018 in U.S. Appl. No. 15/151,252.
USPTO: Office Action dated Nov. 28, 2017 in U.S. Appl. No. 15/189,845.

(56) References Cited

OTHER PUBLICATIONS

USPTO; Notice of Allowance dated Jun. 15, 2018 in U.S. Appl. No. 15/189,845.
USPTO: Notice of Allowance dated Jul. 11, 2018 in U.S. Appl. No. 15/189,845.
USPTO: Office Action dated Nov. 30, 2017 in U.S. Appl. No. 15/189,829.
USPTO; Restriction Requirement dated Nov. 30, 2017 in U.S. Appl. No. 15/214,412.
USPTO: Office Action dated Mar. 5, 2018 in U.S. Appl. No. 15/214,412.
USPTO; Final Office Action dated Aug. 8, 2018 in U.S. Appl. No. 15/214,412.
USPTO; Office Action dated Dec. 11, 2018 in U.S. Appl. No. 15/214,412.
USPTO: Office Action dated Nov. 1, 2017 in U.S. Appl. No. 15/297,698.

* cited by examiner

DISTAL RADIUS PLATE

CROSS-REFERENCE TO RELATED APPLICATIONS

The present application is a continuation of U.S. patent application Ser. No. 15/146,824, filed May 4, 2016, entitled "DISTAL RADIUS PLATE," now issued as U.S. Pat. No. 10,441,330 B2 on Oct. 15, 2019, which claims a priority benefit under 35 U.S.C. § 119(e) of U.S. Provisional Application Ser. No. 62/163,912, filed May 19, 2015, entitled "DISTAL RADIUS PLATE." The entirety of each of the aforementioned applications is hereby incorporated by reference herein.

Any and all applications for which a foreign or domestic priority claim is identified in the Application Data Sheet as filed with the present application are hereby incorporated by reference under 37 CFR 1.57.

FIELD AND BACKGROUND OF THE INVENTION

The forearm has two large bones, the radius and the ulna, which run parallel to one another. The proximal end of the radius is at the lateral side of the elbow and extends all the way to the thumb side of the wrist which is the distal end of the radius (from a reference position in which the palm of the hand faces forward). The radius can also be divided in its other dimensions. For example the palm side of the radius bone is called the "volar" and the other side is called "dorsal." The volar distal radius therefore refers to the palm side of the distal radius. The most prominent region (the part that sticks out like a ridge line) of the volar distal radius is called the "watershed line." A distal radius fracture is a common bone fracture of the distal end of the radius in the forearm.

Surgical implantation of a fixation (called a radius plate herein) plate to secure a broken radius has significantly helped revolutionize treatment of distal radius injuries. The plate may be fixed adjacent to the bone to be healed and is held in place using screws. There are many different techniques for treating distal radius fractures including dorsal plating, fragment specific fixation, non-spanning external fixation, volar plating, spanning internal fixation plates.

Locked volar plating is a commonly used technique that has significantly improved the value of treatment. The volar plate has holes and is affixed by screws that run through holes in the plate.

Notwithstanding its value, a well-known complication of volar plating is irritation and/or rupture of the tendons, especially flexor tendons. The idea is to keep the bone fragments of the fracture together securely without causing irritation or rupture of the tendons. The most common way to position the volar plate is to position it at or just proximal to the watershed line of the distal radius.

Other prior art devices for securing are known that affix solely to the radius. These devices normally have an elongated section that extends along the body part of the radius prior to its distal end near the wrist. At the distal end, which is wider than the body, a plate connected to the elongated portion is affixed, normally by screwing into place.

Some common problems with the aforementioned prior art devices are (1) they are difficult to center on the radius bone, (2) they sometimes rotate out of being centered after first being affixed, (3) they are not shaped like the distal end of the radius and may not secure it properly, and (4) they are not shaped properly, and do not have the proper screw holes or locations, to cover every size arm/hand (or at least a large range of arm/hand sizes).

SUMMARY OF THE INVENTION

As used herein with respect to the radius bone, "body" or "body portion" means the long part of the radius bone extending up the arm from the distal radius. "Distal radius" means the part of the radius bone at its distal end, near the wrist and thumb. The "elongated portion" of a distal radius plate is the portion that is affixed to the body of the radius bone. The "distal radius portion" or "radius portion" of a distal radius plate is the portion that affixes to the distal radius.

There are two aspects of the invention. One is a distal radius plate formed entirely of metal, such as stainless steel. The other is a distal radius plate with a metal support for strength and rigidity, which is overlaid with plastic. The plastic overlay forms, or eliminates the need for, complex shapes that must be machined into the metal, thereby reducing the cost of making and the cost and time to manufacture the distal radius plate.

A distal radius plate according to invention has two basic portions, an elongated portion and a distal radius portion. Each is ergonomically designed to follow the shape of the radius bone. The distal radius portion is asymmetric and follows the outline of the distal radius over preferably 80 percent of its lower-most part. This helps center the entire distal radius plate and better aligns with the radius bone to secure the bone when affixed to it.

A distal radius plate according to aspects of the invention may have a straight line down at least the top surface elongated portion, and preferably along both the elongated and distal radius portion to enable a surgeon to determine quickly when the plate is centered on the radius bone.

When installing a distal radius plate, the incision in the arm/wrist is sometimes small and it can be difficult to determine the exact plate alignment. Therefore, the ability for a surgeon to quickly and accurately center the distal radius plate on the radius bone is desirable.

A distal radius plate according to the invention may also have a stop, which can be a piece of metal attached to the elongated portion and that extends around the side of the plate on the thumb side. This prevents over rotation of the plate. The stop is preferably at the most proximal end of the distal radius plate.

DETAILED DESCRIPTION OF PREFERRED EMBODIMENT

Figure 1:
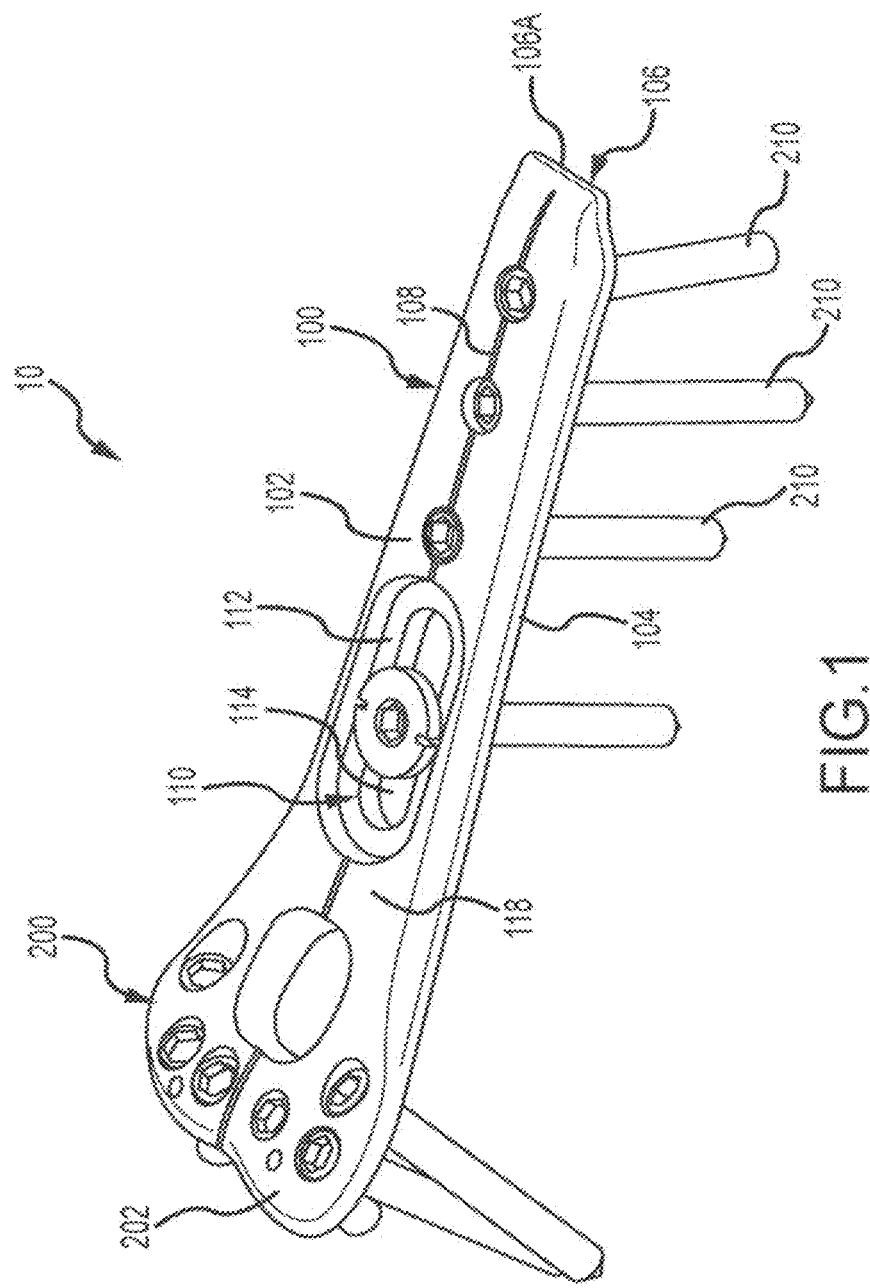
FIG. 1 is a top, perspective view of a device according to aspects of the invention.
Figure 2:
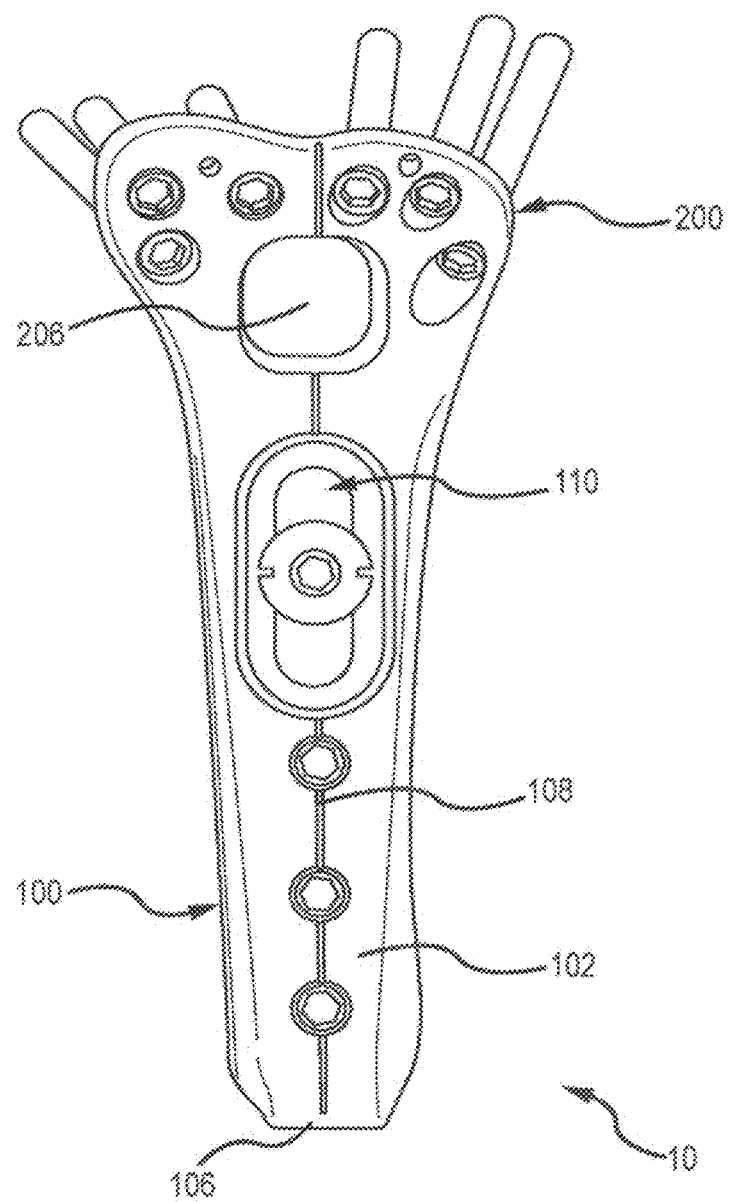
FIG. 2 is a top view of the device of FIG. 1.
Figure 3:
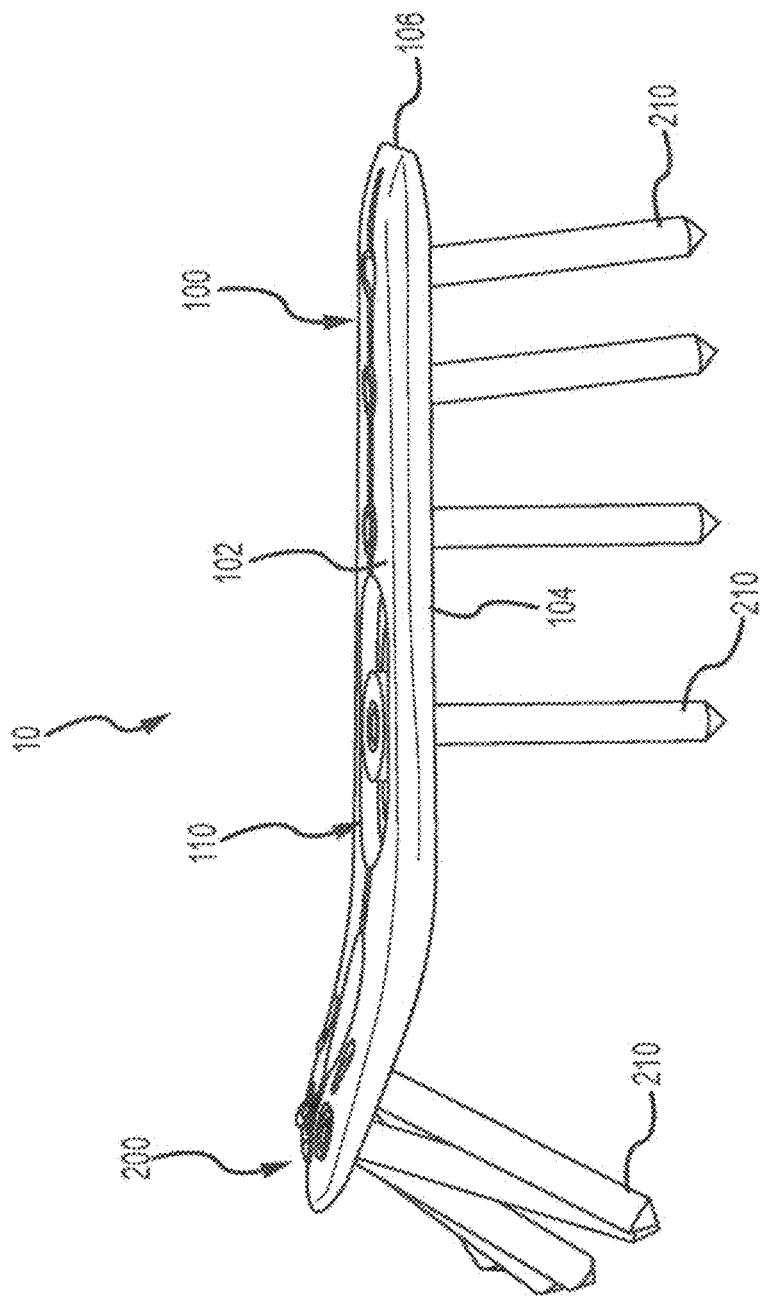
FIG. 3 is a side view of the device of FIG. 1.
Figure 4:
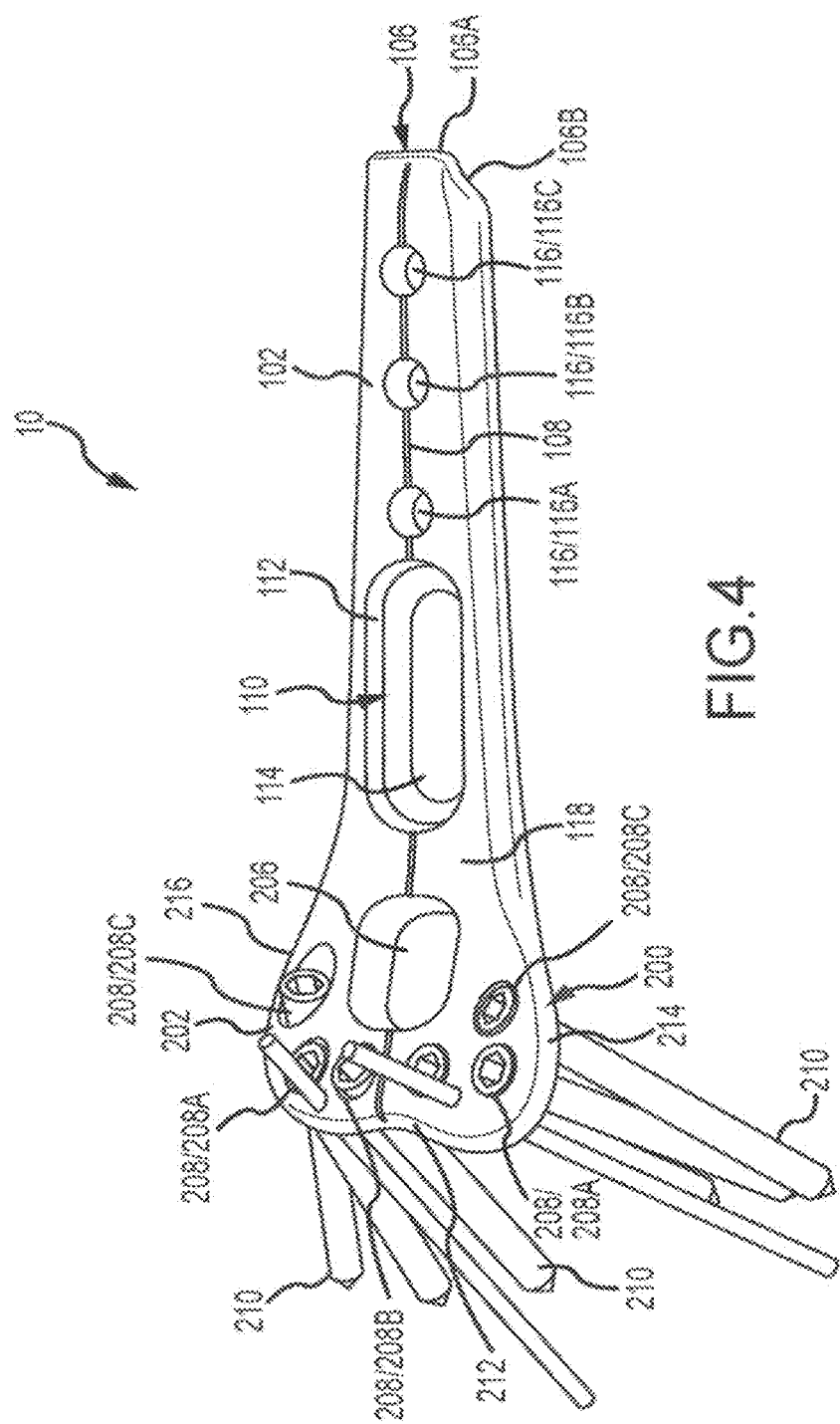
FIG. 4 is a top perspective view of the device of FIG. 1.
Figure 5:
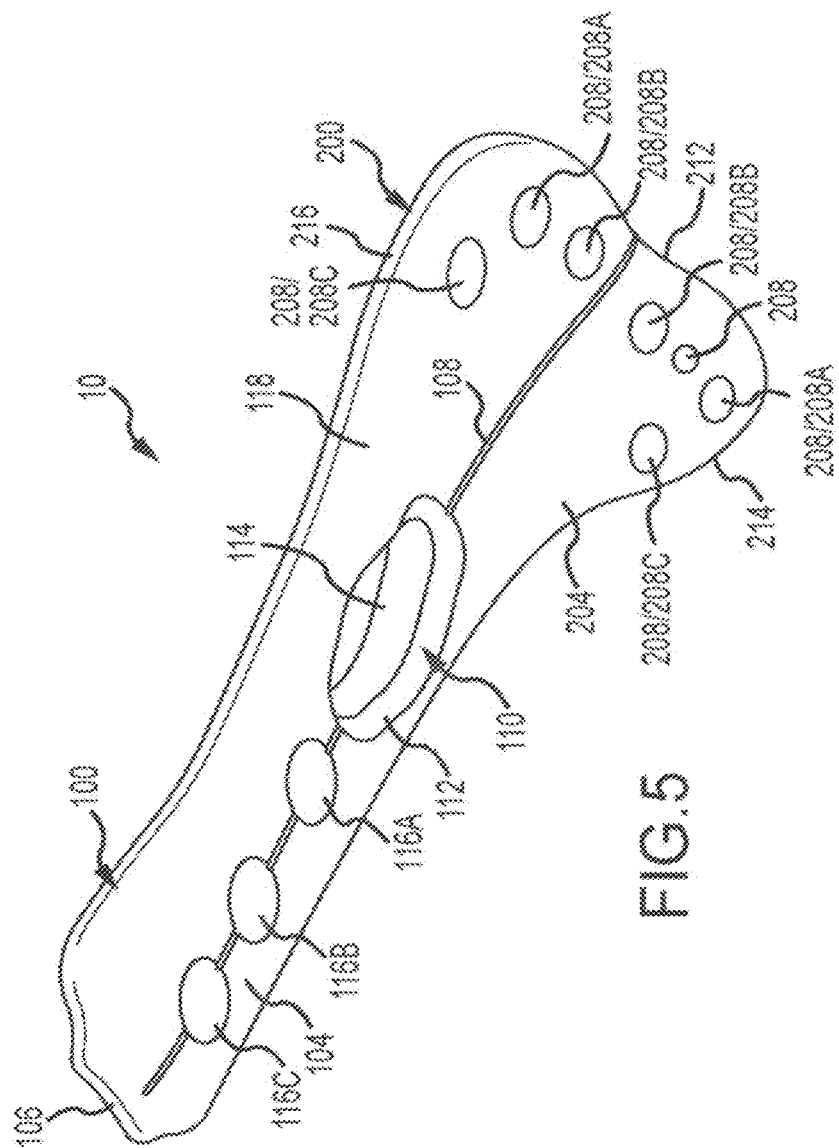
FIG. 5 is a bottom perspective view of the device of FIG. 1.
Figure 6:
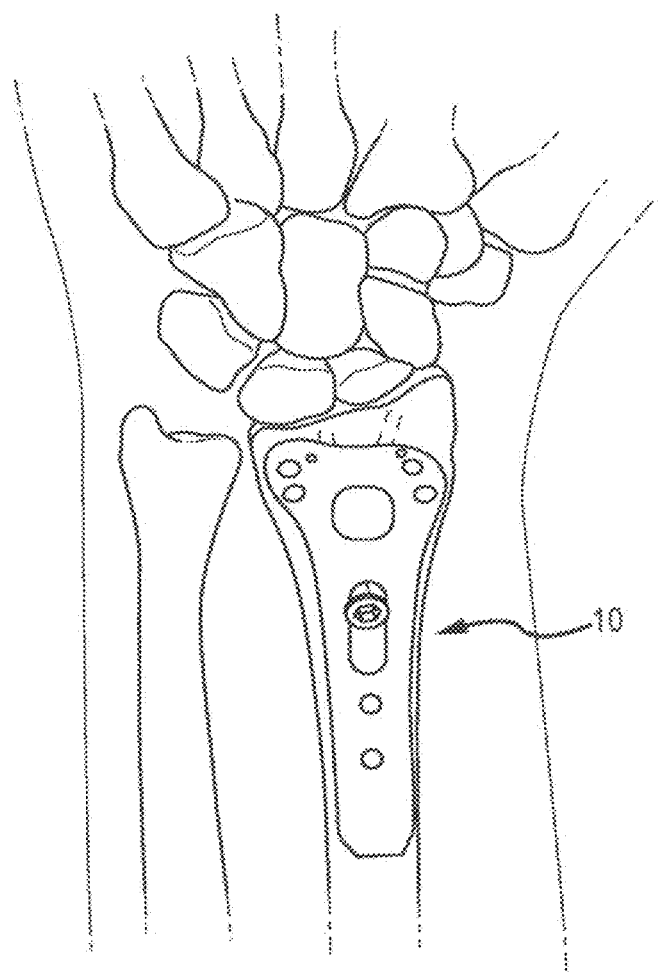
FIG. 6 is a top, x-ray view of the device of FIG. 1 attached to a radius bone.
Figure 7:
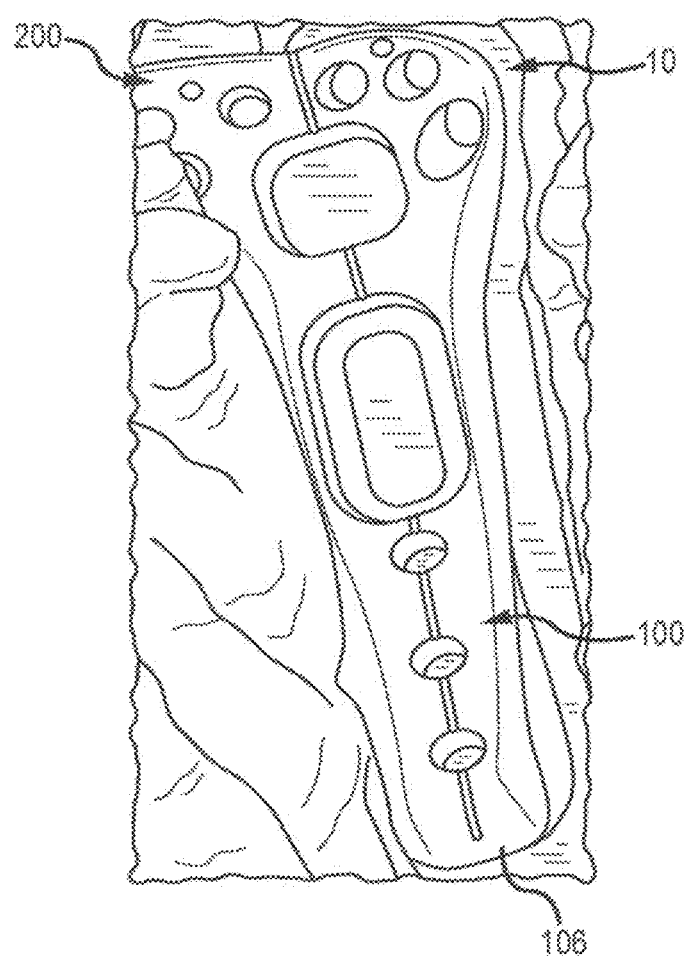
FIG. 7 is a top view of the device of FIG. 1 attached to a radius bone.

Turning now to the drawings wherein the purpose is to describe a preferred embodiment of the invention and not to limit same. FIG. 1 shows a top, perspective view of a distal radius plate 10 in accordance with aspects of the invention. Distal radius plate 10 is preferably comprised of metal, such as stainless steel. Plate 10 has two main portions: elongated portion 100 and distal radius portion 200. Elongated portion 100 has a top side 102, a bottom side 104 and a distal end (or end) 106. Top side 102 is smooth and has a centerline 108 stamped or otherwise formed therein, or centerline 108 could be printed. A slot 110 is formed in portion 100 and has an upper opening 112, which is large enough to receive and retain a screw head, and a lower opening 114, which is large enough for a screw body to pass through and thread into the body of the radius bone, but too small for the screw head to pass through.

Between slot 112 and end 106 are three first openings 116 shown as being centered in elongated portion 100. Although three openings 116 are shown, one or more first openings 116 may be utilized. The purpose of openings 116 is for screws to pass through and screw into the radius body thus affixing elongated portion 100 to the elongated body. Openings 116 are preferably formed at angles so that openings 116A and 116C are skewed in one direction by 5°-10°, and preferably 10°, or from 5°-20°. Opening 116B is preferably skewed in the opposite direction by the same amount. This skewing forces the screws going through the respective openings to enter the radius body at different angles, which makes it more difficult for the elongated portion 100, and distal radius plate 10, from rotating.

End 106 is tapered to a rounded edge 106A and has an inner stop 106B that prevents it from rotating on the radius body. Stop 106B is shaped like a hook so if the distal radius plate rotates, the outer edge of the stop presses against the body of the radius bone preventing further rotation.

Bottom side 104 is concave to more easily be fit to and centered on the radius body.

There is preferably an intermediate section 118 with an elongated portion 100 and the distal radial portion 200. Intermediate portion also widens into portion 200. Considering the upward bend in the intermediate portion 118, portion 200 is preferably about ¼" to ½" offset from (or higher than) elongate portion 100.

Distal radius portion 200 is wide relative elongated portion 100 and is preferably shaped to approximate the shape of the distal radius part of the radius bone. As used herein, the distal radius portion refers to the lower most portion of the radius bone, which is near the wrist. Portion 200 is lower on the radius bone and arm when installed.

Portion 200 has a top surface 202, a bottom surface 204, an aperture 206 and a plurality of second openings 208. Openings 208 as shown are in three sets formed at three different angles. There is a first set 208A (for large distal radiuses), a second set 208B for smaller distal radiuses and a third set 208C for further anchoring to a distal radius of appropriate sizes. Fasteners 210 fit through the respective openings and are affixed to the distal radius preferably by being threaded into the bone and the fastener heads are countersunk into the openings. A surgeon can determine which openings to place fasteners through depending on the size of the distal radius. Further, the angles of the second openings may permit the fasteners to crisscross, which provides compressive strength.

Portion 200 has an end 212, a side 214, and a side 216. End 212, side 214 and side 216 are preferably the same shape of the distal radius for at least 50% of the distance from portion 100 moving towards end 212, or for at least 75% of the distance from portion 100 moving towards end 212, or for at least 80% of the distance from portion 100 moving towards end 212.

The distal radius plate according to various aspects of the invention can be quickly centered and attached, and one size fits most or all radius bones.

In use, an opening is made in the arm and the distal radius plate is centered on the radius bone using concave surface 104 and centerline 108. Then a fastener is positioned through slot 110 and screwed into the radius body. Distal radius plate 10 can be moved back and forth along slot 110 to properly position portion 200 over the distal radius. The slot also permits limited side-to-side movement to center the distal radius plate.

Figure 8:
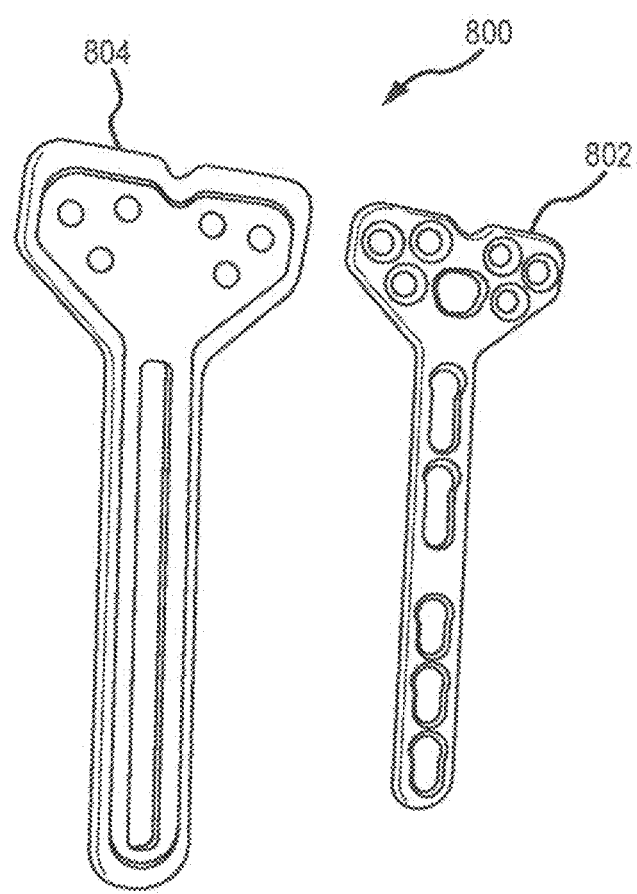
FIG. 8 shows top views of a metal support and plastic overlay that can be used to form a different embodiment of the invention.
Figure 9:
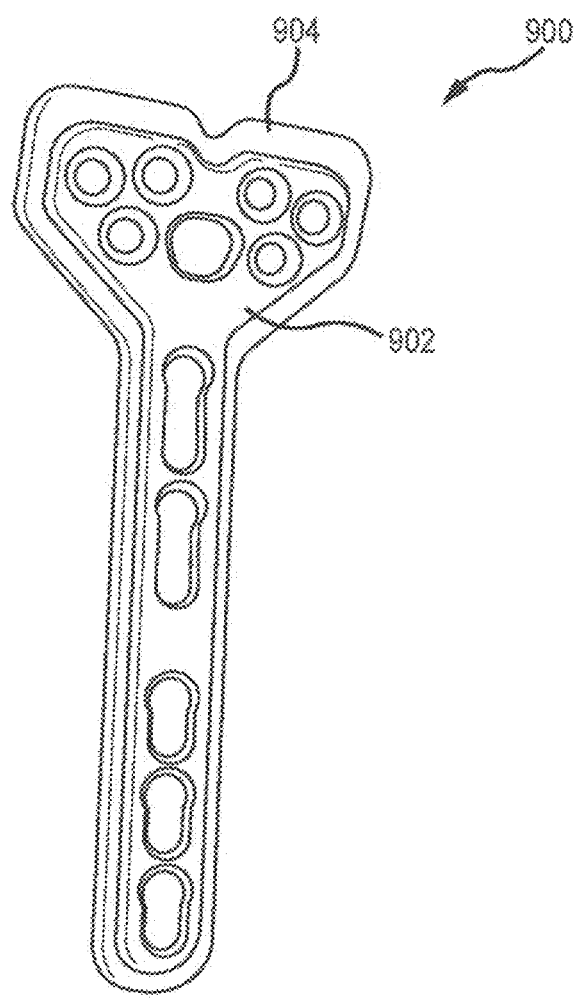
FIG. 9 shows the plastic overlay of FIG. 8 attached to a metal support.

In another embodiment shown in FIGS. 8 and 9, a distal radius plate according to the invention has a metal support and plastic overlay. The metal support preferably comprises steel, such as stainless steel. The plastic overlay can be comprised of any suitable material, such as PEEK. The advantage of the plastic overlay is that it reduces production time and costs little or no complex machining of the metal need be performed. Specific embodiments of a distal radius plate with a plastic overlay are described below and shown in some of the attached drawings.

By using a plastic overlay, the metal support can simply be stamped using a stamping tool. The smooth edges, the distal edge of the elongated portion and the shape of the distal radius portion can be formed in the plastic made by an injection molding process or another suitable process. Furthermore, the first openings and second openings need not be machined at angles—they can be punched straight through the metal support. The plastic can partially fill the openings and a surgeon can thread a fastener through the plastic and into the radius bone at any angle he/she desires.

A plastic overlay may be manufactured separately and attached to the metal support, for example, by pressure fitting them together. Or, the plastic may be formed over the metal support.

Having thus described preferred embodiments of the invention, other variations and embodiments that do not depart from the spirit of the invention will become apparent to those skilled in the art. The scope of the present invention is thus not limited to any particular embodiment, but is instead set forth in the appended claims and the legal equivalents thereof. Unless expressly stated in the written description or claims, the steps of any method recited in the claims may be performed in any order capable of yielding the desired result.

Some specific, exemplary embodiments of the invention are described below.

1. A distal radius plate having:
   (a) an elongated portion with one or more first openings, the elongated portion for being attached to the body portion of the radius bone; and
   (b) a distal radius portion with one or more second openings, wherein at least some of the openings are formed at outward angle; wherein screws passing through the one or more first openings are received in the body portion and screws passing through the one or more second openings are received in the distal radius.

2. The distal radius plate of example 1 wherein there is a upward bend between the elongated portion and the radius portion.

3. The distal radius plate of example 2 wherein the radius portion is ¼" to ½" above the elongated portion.

4. The distal radius plate of any of examples 1-3 that includes a slot in the elongated portion, the slot for receiving a screw to anchor and center the elongated portion on the body portion.

5. The distal radius plate of example 4 wherein the slot is between ½" and 1½" in length.

6. The distal radius plate of any of examples 1-5 wherein there are multiple first openings.

7. The distal radius plate of example 6 wherein the elongated portion has an end distal the distal radius portion and an end proximal the distal radius portion and each of the first openings is between the distal end and the slot.

8. The distal radius plate of any of examples 1-7 wherein the elongated portion has a visible center line to assist in centering the distal radius plate on the radius bone.

9. The distal radius plate of any of examples 1-8 wherein the elongated portion has an end distal the distal radius portion and the distal end is tapered to form a rounded edge.

10. The distal radius plate of any of examples 1-9 wherein the distal radius portion has different second openings formed at different angles in order to accommodate different-sized distal radiuses.

11. The distal radius plate of any of examples 1-10 wherein the distal radius portion has an enlarged opening between the second openings and the elongated portion.

12. The distal radius plate of example 10 wherein there is a first set of second openings to fit one sized hand and a second set of second openings to fit a different sized hand, wherein the first set of second openings are formed at different angles than the second set of second openings.

13. The distal radius plate of any of examples 1-12 wherein each of the second openings has a locking mechanism to hold a fastener in place.

14. The distal radius plate of any of examples 1-13 wherein the shape and size of the distal radius portion enables it to self center on the distal radius bone.

15. The distal radius plate of any of examples 1-13 wherein the distal radius portion has the shape of the distal radius.

16. The distal radius plate of any of examples 1-15 wherein the at least two second openings are positioned such that at least one bone portion in the distal radius can be engaged by at least two fasteners.

17. The distal radius plate of any of examples 1-15 wherein the second openings are positioned such that more than one bone portion in the distal radius can be engaged by more than one fastener.

18. The distal radius plate of any of examples 1-17 wherein the elongated portion has a top surface, and a bottom surface that rests against the body of the radius bone, the bottom surface being concave.

19. The distal radius plate of any of examples 1-18 wherein the elongated portion has an end distal the distal radius portion and the distal end has a flange.

20. The distal radius plate of any of examples 1-19 wherein there is a first set of second openings to fit one sized hand and a second set of second openings to fit a different sized hand, wherein the first set of openings are positioned farther from the center of the distal radius portion than the second set of openings.

21. The distal radius plate of any of examples 1-20 wherein at least the upper half of the distal radius portion is shaped the same as the distal radius bone.

22. The distal radius plate of any of examples 1-20 wherein at least the upper 75% of the distal radius portion is shaped the same as the distal radius.

23. The distal radius plate of any of examples 1-22 wherein the bottom of the elongated portion has a stop including a ridge to prevent rotation.

24. The distal radius plate of example 23 wherein the stop is at the end of the elongated portion distal from the distal radius portion.

25. The distal radius plate of example 4 wherein the slot accepts a screw that is threaded into the radius bone body and the distal radius plate can slide along the radius bone with the screw maintaining the side-to-side position of the distal radius plate.

What is claimed is:

1. A method of stabilizing a fractured radius of a patient using a plate that comprises an elongated portion and a distal radius portion, the method comprising:
   centering the plate on the radius bone using a visible centerline positioned on the elongated portion of the plate;
   attaching the elongated portion of the plate to an elongated body part of the fractured radius using a fastener including a stem with a first diameter and a head with a second diameter that is greater than the first diameter, the elongated portion comprising a slot that includes an upper opening sized to receive the head of the fastener and a lower opening sized to receive the stem of the fastener without allowing passage of the head of the fastener therethrough, wherein the stem of the fastener extends through the slot into the elongated body part of the fractured radius and the head is retained in the upper opening so as to anchor the elongated portion of the plate on the radius bone and to allow the plate to move lengthwise and side-to-side to be adjusted relative to the radius bone;
   affixing the elongated body portion to the body part of the fractured radius using one or more first fixation devices through one or more first openings in the elongated portion; and
   affixing the distal radius portion of the plate to a distal radius part of the fractured radius using one or more second fixation devices through one or more second openings in the distal radius portion of the plate.

2. The method of claim 1, wherein at least two of the first openings are skewed in generally opposite directions so as to force the first fixation devices through the respective first openings to enter the elongated body part of the fractured radius at different angles.

3. The method of claim 1, wherein the elongated portion comprises a free end further away from the distal radius portion and an opposite end closer to the distal radius portion, and each of the first openings is between the free end and the slot.

4. The method of claim 1, wherein the slot is between ½" and 1½" in length.

5. The method of claim 1, wherein the plate comprises a bend extending from the elongated portion to the distal radius portion.

6. The method of claim 1, wherein the distal radius portion comprises a first set of second openings to fit a fractured radius of a first size and a second set of second openings to fit a fractured radius of a second size that is different from the first size.

7. The method of claim 6, wherein the first set of second openings are formed at different angles than the second set of second openings.

8. The method of claim 1, wherein the distal radius portion comprises a shape and size that enables the distal radius portion to self-center on a distal radius part of the fractured radius.

9. The method of claim 1, wherein more than one of the second openings are positioned such that more than one area in the distal radius part are engaged by more than one second fixation devices.

10. The method of claim 1, wherein the elongated portion comprises a top surface and a bottom surface, the bottom surface configured to rest against the elongated body part of the fractured radius, and the bottom surface being concave.

11. The method of claim 10, wherein the bottom surface of the elongated portion comprises a stop including a ridge to prevent rotation.

12. The method of claim 11, wherein the stop is at a free end of the elongated portion.

13. The method of claim 10, wherein the visible centerline is located on the top surface.

14. A method of stabilizing a fractured radius of a patient using a plate, the method comprising:
centering the plate on the radius bone using a visible centerline positioned on the plate;
attaching the plate to an elongated body part of the fractured radius using a fastener including a stem with a first diameter and a head with a second diameter that is greater than the first diameter, the plate comprising a slot that includes an upper opening sized to receive the head of the fastener and a lower opening sized to receive the stem without allowing passage of the head of the fastener therethrough, wherein the stem of the fastener extends through the slot into the elongated body part of the fractured radius and the head is retained in the upper opening so as to anchor the plate on the radius bone and to allow the plate to move lengthwise and side-to-side to be adjusted relative to the radius bone; and
affixing the plate to the fractured radius using a plurality of fixation devices through a plurality of openings located on the plate and proximal and distal of the slot.

15. The method of claim 14, wherein the slot is between ½" and 1½" in length.

16. The method of claim 14, wherein the plate comprises a bend extending from an elongated portion to a distal radius portion.

17. The method of claim 16, wherein the slot is located on the elongated portion.

18. The method of claim 14, wherein the plurality of openings distal of the slot comprises a first set of openings to fit a fractured radius of a first size and a second set of openings to fit a fractured radius of a second side different from the first size.

19. The method of claim 18, wherein the first and second sets of openings are formed at different angles.

20. The method of claim 14, wherein at least two of the plurality of openings are skewed in generally opposite directions so as to force the plurality of fixation devices to enter the fractured radius at different angles.

* * * * *